United States Patent
Higashi et al.

(10) Patent No.: US 7,978,331 B2
(45) Date of Patent: Jul. 12, 2011

(54) ATTENUATED TOTAL REFLECTION OPTICAL PROBE AND APPARATUS THEREWITH FOR SPECTROSCOPIC MEASUREMENT OF AQUEOUS SOLUTION

(75) Inventors: Noboru Higashi, Osaka (JP); Yukihiro Ozaki, Hyogo (JP); Akifumi Ikehata, Hyogo (JP)

(73) Assignee: Kurashiki Boseki Kabushiki Kaisha, Kurashiki-shi (JP)

( * ) Notice: Subject to any disclaimer, the term of this patent is extended or adjusted under 35 U.S.C. 154(b) by 208 days.

(21) Appl. No.: 12/293,061

(22) PCT Filed: Mar. 8, 2007

(86) PCT No.: PCT/JP2007/054548
§ 371 (c)(1),
(2), (4) Date: Sep. 15, 2008

(87) PCT Pub. No.: WO2007/108328
PCT Pub. Date: Sep. 27, 2007

(65) Prior Publication Data
US 2009/0073436 A1    Mar. 19, 2009

(30) Foreign Application Priority Data
Mar. 16, 2006 (JP) .................... 2006-073073

(51) Int. Cl.
*G01N 21/55* (2006.01)
(52) U.S. Cl. .................... 356/445; 356/301
(58) Field of Classification Search .......... 356/445, 356/301
See application file for complete search history.

(56) References Cited

U.S. PATENT DOCUMENTS
5,097,130 A    3/1992    Koashi et al.
(Continued)

FOREIGN PATENT DOCUMENTS
EP        503236 A2 *  9/1992
(Continued)

OTHER PUBLICATIONS
Higashi et al., "Potential of Far-Ultraviolet Absorption Spectroscopy as a Highly Sensitive Quantitative and Qualitative Analysis Method for Aqueous Solutions, Part I: Determination of Hydrogen Chloride in Aqueous Solutions" Applied Spectroscopy vol. 58, No. 8 (2004) 910-916.
(Continued)

*Primary Examiner* — Tarifur R. Chowdhury
*Assistant Examiner* — Isiaka O Akanbi
(74) *Attorney, Agent, or Firm* — Birch, Stewart, Kolasch & Birch, LLP (57) ABSTRACT

An optical probe consists of a first component made of a first optical material having a light transmission property in the far ultraviolet region, and a second component made of a second optical material arranged in contact with the surface of the first component. For example, the second optical material has a higher refractive index in the far ultraviolet region than the first optical material. The second component is provided, on a side in contact with a sample, with a surface totally reflecting light having incident angle equal to or larger than the critical angle. Alternatively, an optical probe has an optical material having a light transmission property in the far ultraviolet region, having a surface totally reflecting a ray of light of incident angle equal to or larger than the critical angle, at a side in contact with a sample, and the refractive index is higher near the surface than at the other parts in the far ultraviolet region. Consequently, a spectroscopic measurement becomes possible on very small solute components dissolved into water or the like in the far ultraviolet region.

13 Claims, 10 Drawing Sheets

U.S. PATENT DOCUMENTS

| | | | |
|---|---|---|---|
| 5,220,403 A * | 6/1993 | Batchelder et al. | 356/450 |
| 5,434,411 A * | 7/1995 | Miyahara et al. | 250/339.07 |
| 5,434,663 A | 7/1995 | Maule | |
| 5,703,366 A | 12/1997 | Sting et al. | |
| 5,822,073 A * | 10/1998 | Yee et al. | 356/445 |
| 6,330,062 B1 * | 12/2001 | Corn et al. | 356/445 |
| 6,421,128 B1 * | 7/2002 | Salamon et al. | 356/445 |
| 6,570,657 B1 * | 5/2003 | Hoppe et al. | 356/445 |
| 6,907,390 B1 | 6/2005 | Reffner et al. | |

FOREIGN PATENT DOCUMENTS

| | | |
|---|---|---|
| JP | 62-75230 A | 4/1987 |
| JP | 64-56401 A | 3/1989 |
| JP | 3-175341 A | 7/1991 |
| JP | 5-332920 A | 12/1993 |
| JP | 5-509402 A | 12/1993 |
| JP | 7-12716 A | 1/1995 |
| JP | 8-75639 A | 3/1996 |
| JP | 10-82738 A | 3/1998 |
| JP | 2001-91710 A | 4/2001 |
| JP | 2005-106712 A | 4/2005 |
| JP | 2005-214863 A | 8/2005 |
| JP | 2005-233884 A | 9/2005 |
| WO | WO-92/03720 A1 | 3/1992 |
| WO | WO-2006/109408 A1 | 10/2006 |

OTHER PUBLICATIONS

Extended Search Report dated Nov. 11, 2010 for corresponding EPO 07738039.2.

* cited by examiner

REFRACTIVE INDEX PROFILE

ATTENUATED TOTAL REFLECTION OPTICAL PROBE AND APPARATUS THEREWITH FOR SPECTROSCOPIC MEASUREMENT OF AQUEOUS SOLUTION

TECHNICAL FIELD

The invention relates to spectroscopic analysis in the far ultraviolet region.

BACKGROUND ART

Recently it is needed more and more to measure the purity of water and very weak change in a property of water precisely without changing the quality of water. For example, in a fabrication process of a semiconductor, the water purity is required to have a level of specific resistivity near the theoretical limit. Further, so-called functional water, wherein a specified function is added to ultrapure water having very high purity, is used recently.

Spectroscopic analysis is used very effectively for qualitative and quantitative analysis of water and aqueous solutions in various ways. The spectroscopy is classified into ultraviolet and visible spectroscopy, near infrared spectroscopy and infrared spectroscopy according to measurement wavelength region.

In near infrared spectroscopy, absorption spectra of water due to hydrogen bonds inherent to water are observed remarkably in 800 to 1400 nm. It is proposed in, for example, Japanese patent laid open Publication H3-175341 to use the spectra for measuring solute components in water. In the liquid state water molecules are bonded to each other with hydrogen bonds between them, and the state of hydrogen bonds are changed sensibly when solute components are mixed into water. By studying the change, the mixed components can be analyzed quantitatively. In concrete, when an inorganic electrolyte is dissociated as ions in water, bonding states of water molecules themselves and those between water molecules are affected due to, for example, cutting or distortion of hydrogen bonds between water molecules around an ion and a bulk water molecule caused by hydration of ions, polarization of water molecules due to electric fields of ions, and the like. Then, the near infrared spectra of the aqueous solution become different from those of pure water. By calibrating the change in spectra beforehand, the concentrations of the ion species can be determined quantitatively based not on the absorption spectra due to the ion species, but on the change in absorption spectra of water.

Recently, it is proposed to measure the concentration of hydrated substances in an aqueous solution quantitatively with far ultraviolet spectra of water which is closely related to the bonding state of water as in near infrared spectra (Japanese Patent laid open Publication 2005-214863 and APPLIED SPECTROSCOPY Vol. 58, No. 8 (2004) 910-916). In order to discriminate an aqueous solution and to measure very small concentrations of solutes quantitatively, the method uses that absorption spectra due to n→σ* transition of water having a peak around 150 nm shifts toward the longer wavelength side due to the electric field formed between water itself and hydrated ions in the solution, and that a part of the spectra appears in a region which can be measured with a conventional spectroscopic apparatus (or a spectroscopic apparatus which does not need evacuation). The absorption spectra of water in the far ultraviolet region has a much higher sensitivity for detection and for quantitative analysis on very small solute concentrations, but it is used only in an a wavelength range longer than 180 nm or a limit of absorption spectra measurement because the absorbance of water itself is very large.

Attenuated total reflectance (ATR) is explained below because it is used in the invention in order to measure absorption spectra of a material having very large absorption. According to an attenuated total reflectance method, penetration of light of the order of wavelength (evanescent wave) on total reflectance at the surface of an optical probe is measured, and absorption spectra in correspondence to a cell length of the order of wavelength can be obtained. In Japanese Patent laid open Publication S62-75230 a method is proposed for measuring solutions with high solute concentrations with an optical probe for attenuated total reflection spectra. Various attenuated total reflectance methods have been used by using an optical probe made of synthetic quartz, sapphire or the like. In Japanese Patent laid open Publication H7-12716 it is proposed to enhance measurement sensitivity of the attenuated total reflection method itself.

An optical probe for attenuated total reflectance made of a plurality of optical materials is also proposed. In an infrared optical system for optical analysis proposed in the U.S. Pat. No. 5,703,366, an optical probe reflects a light totally in a plane in contact with a sample substance. In order to overcome disadvantages of a probe made of one crystal member, such as chemical resistance, mechanical properties or high cost, a probe has a first crystal member and a second crystal member in contact with the first one. The second crystal member has a plane in contact with a sample substance. The two crystal members have substantially the same refractive index. For example, if the second crystal member is diamond which transmits infrared light, the first crystal member is, for example, zinc selenide (ZnSe).

In an optical element for transmitting infrared light described in Japanese Patent laid open Publication S64-56401/1989, a diamond thin film or a diamond-like carbon (DLC) thin film including a diamond structure of, for example, 600 nm thickness is formed on a surface of an optical element made of a material such as $SiO_2$ or ZnSe which transmits infrared light, in order to improve the surface strength and humidity resistance. One example of the optical element is a multi-reflection prism provided in an attachment for an apparatus for attenuated total reflection measurement. As to the optical properties of a DLC thin film used in the embodiment, it is only stated that the infrared absorption spectra are not affected, except results on abrasion test and humidity resistance. That is, only mechanical and chemical properties attract attention on the function of a diamond thin film.

Further, in a method described in Japanese Patent laid open Publication H5-332920/1993, an analysis surface of a sample (silicon wafer) is arranged to contact with air, while the opposite surface thereof is closely attached to a prism made of a soft solid material having refractive index smaller than that of the sample. Then, an infrared ray of light is incident on the solid material to be reflected at the analysis surface, and attenuated total reflection spectra are measured at the sample surface having refractive index larger than the prism material. In this method, it is supposed that the second layer (sample) in the composite materials transmits infrared light.

It is proposed on an attenuated total reflection optical probe, in Japanese Patent laid open Publication 2001-91710, that a second layer having large optical absorption, such as zinc oxide or tin dioxide, has mirror adhesion to a transparent first layer such as silicon. The second layer contacts with a sample. An optical material having a larger refractive index is used for the first layer, and another optical material having a smaller refractive index is used for the second layer. However, if the end face angle and incident angle described in the first embodiment and the like are used, the ray of light incident on the first layer is reflected totally at the interface between the first and second layers, or only a part of the evanescent waves can penetrate into the sample located at a side of the second layer opposite to the interface. Further, because the optical absorption of the second layer is large, absorption can be measured with a very low signal-to-noise ratio eventually. The concept of this probe is not clear.

As explained above on the prior art prisms made of a plurality of optical materials, it has been considered that an attenuated total reflection prism can be fabricated only if the refractive index of a second layer in contact with a sample is equal to or larger than that of a first layer. In any probe, it is supposed that the refractive index of a sample in contact with the interface of the composite prism is smaller than that of the first layer in the prism. The optical materials are selected under a condition that they transmit light such as infrared light. Japanese Patent laid open Publication 2001-91710 describes an example of a composite prism wherein the refractive index of the second layer is smaller than that of the first layer. In this case, the attenuated total reflection occurs at the interface between the first and second layers, and total reflection spectra at the sample surface cannot be measured. The concept of this probe is not clear.

Absorption of water in the near infrared region is weak because it is due to an inherently forbidden transition, and very small solute concentrations in water cannot be measured. Therefore, a method is needed for measuring such very small solute concentrations which cannot be measured in near infrared spectra. On the other hand, water has a large absorption peak near 150 nm, and solutes can be detected and their concentrations can be measured due to a change in the absorption spectra at a much higher sensitivity than that of near infrared spectra. However, when spectra of water or an aqueous solution is measured in far ultraviolet region, the absorption of water is a large obstacle for spectroscopy. As to other substance than water having large absorption in the far ultraviolet region, the absorption becomes a large obstacle for spectroscopic measurement similarly. The above-mentioned attenuated total reflection measurements for the infrared and visible regions cannot be used in the far ultraviolet region because transmittance is not sufficient high or because the optical probe does not cause total reflection at the flat plane in contact with a sample substance.

DISCLOSURE OF INVENTION

An object of the invention is to make it possible to measure optical spectra in a far ultraviolet region equal to or smaller than 180 nm so that very small solute components in an aqueous solution or the like can be detected at a high sensitivity or can be analyzed quantitatively.

Attenuated total reflection optical probes are proposed below for measuring an aqueous solution in the far ultraviolet region.

A first attenuated total reflection optical probe according to the invention has a first component made of a first optical material transparent in a far ultraviolet region and having refractive index lower than a medium to be measured as a sample substance, and a second component having an interface in contact with the first component and a flat plane in contact with the sample substance, the second component being made of a second optical material having a transmittance lower than the first component in the far ultraviolet region and having refractive index higher than the medium to be measured. The interface between the first and second components has a form at which light transmitting the first component enters the second component and is incident on the flat plane of the second component at an incident angle equal to or larger than the critical angle. Thus, as the refractive index of the sample substance is smaller than that of the second optical material, total reflection occurs at the flat plane in contact with the sample substance even when the refractive index of the first optical material is larger than that of the sample substance.

In the first attenuated total reflection optical probe, for example, the flat plane in contact with the sample substance and the interface between the first and second components are parallel to each other. Preferably, the first attenuated total reflection optical probe further has a third component made of a third optical material transparent in the far ultraviolet region, wherein the third component is positioned opposite to the first component relative to the second component. In the first attenuated total reflection optical probe, for example, the interface is semicircular. Further, in the first attenuated total reflection optical probe, for example, the interface has an in-coming plane through which a ray of light incident on the plane transmits, and an out-going plane through which a light reflected at the plane transmit. In the first attenuated total reflection optical probe, for example, the flat plane and the interface of the second component are perpendicular to each other.

In the attenuated total reflection optical probe, preferably, the first optical material is selected in a group of magnesium fluoride, lithium fluoride and calcium fluoride, and the second optical material is selected in a group of synthetic quartz, natural quartz, sapphire, zinc selenide and diamond.

In the first attenuated total reflection optical probe, preferably, the interface between the first and second components has a shape. The light transmitting the first component is incident normally to the second component and the light reflected totally at the plane is incident normally when it enters from the second component to the first component.

A second attenuated total reflection optical probe according to the invention is made of an optical material having light transmission property in a far ultraviolet region, wherein the refractive index thereof varies continuously at least in a part thereof. The probe has a flat plane on which incident light at an incident angle equal to or larger than the critical angle is reflected, and refractive index in the far ultraviolet region in a first portion including a part of the flat plane is higher than that of the other portion and that of the sample substance. The optical material is selected, for example, in a group of magnesium fluoride, lithium fluoride and calcium fluoride, and the portion wherein the refractive index varies is formed with diffusion or injection of impurity ions.

Preferably, the first or second attenuated total reflection optical probe further has a coating layer such as a thin film of synthetic quartz, natural quartz or diamond on the plane of the probe in contact with water, the coating layer having thickness smaller than measurement wavelength.

A spectrometer for an aqueous solution according to the invention has one of the above-mentioned attenuated total reflection optical probes, a light source irradiating far ultraviolet light towards the probe, an optical sensor for detecting light totally reflected from the probe, and a spectroscopic element for far ultraviolet light, provided in an optical path from the light source and the optical sensor. Oxygen in the optical path is replaced with gas not absorbing in the ultraviolet region or evacuated in the vacuum state.

It is an advantage of the invention that optical spectra in the far ultraviolet region can be measured for a substance having high absorbance in the far ultraviolet region. Thus, very small solute components in an aqueous solution or the like can be measured at a high sensitivity or analyzed quantitatively easily.

BEST MODE FOR CARRYING OUT THE INVENTION

Embodiments of the invention will be explained with reference to the appended drawings.

Figure 1:
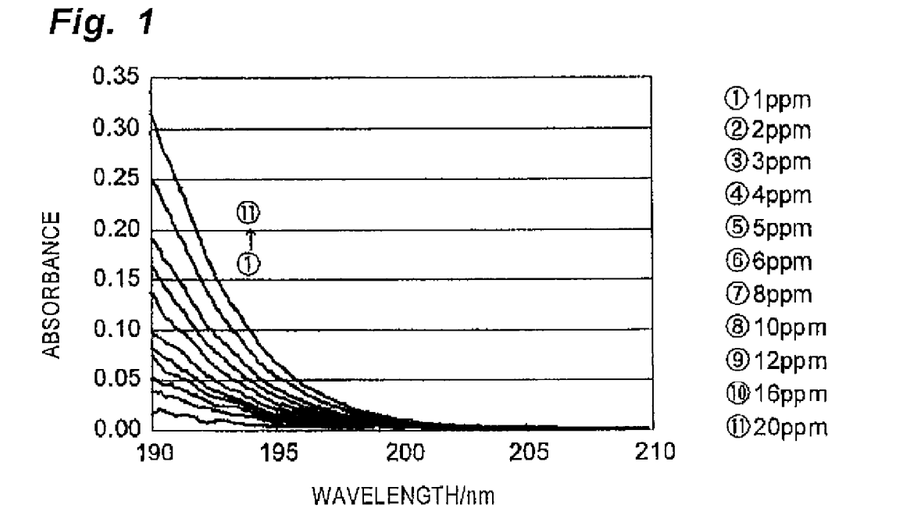
FIG. 1 is a graph of far ultraviolet spectra of an HCl aqueous solution.
Figure 2:
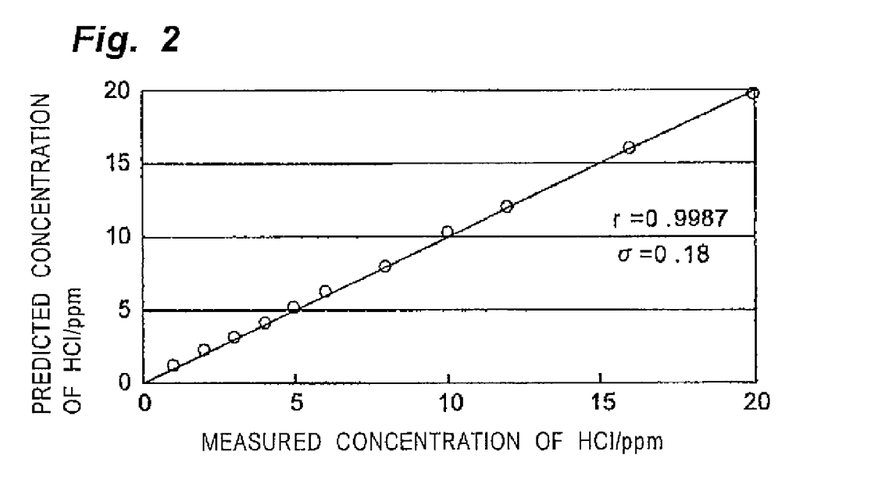
FIG. 2 is a graph on correlation of a calibration model for predicting HCl concentration.

Absorption spectra of water in the near infrared region are weak because they are ascribed to an inherently forbidden transition, and a very small concentration of a solute component cannot be measured. Then, the inventors paid attention to far ultraviolet spectra and found that pure water has a very large, sharp absorption peak around 150 nm in the far ultraviolet region and that a very small concentration of a solute hydrated in an aqueous solution can be measured by measuring a change in a side portion of sharp peak. That is, the absorption of water itself in absorption spectra decreases steeply from the absorption peak around 150 nm to an absorption bottom around 200 nm, and the peak position and the band width thereof are changed due to hydration of a very small concentration of a solute component. Therefore, a slight wavelength shift of the absorption peak is detected at high precision in the side or slope of the absorption peak, and it can be used for a measurement for a very small concentration of a solute in an aqueous solution. (Refer to Japanese Patent laid open Publication 2005-214863.) Thus, a very small concentration of a solute component can be measured by measuring the spectra of the side portion of the absorption peak of water and by creating a calibration line with a multivariate analysis of absorbance measured at a plurality of wavelengths. For example, FIG. 1 shows far ultraviolet spectra of HCl aqueous solutions at eleven concentrations in a range of 0 to 20 ppm (1, 2, 3, 4, 5, 6, 8, 10, 12, 16 and 20 ppm), and FIG. 2 shows correlation of a calibration line model for measuring HCl concentration. The correlation factor R and the standard deviation σ of the model is 0.9987 and 0.18 ppm, respectively. It is found that a very small amount of HCl can be measured at a high precision at least up to 100 ppm. The detection limit of HCl in an aqueous solution is 0.5 ppm in this example.

In the above-mentioned example of measurements on water and aqueous solutions, the wavelengths for measurement are limited to a side portion of the absorption peak of water from 180 to 210 nm because it is considered there would be experimental difficulties when transmittance spectra are measured at wavelengths equal to less than 180 nm. For example, because the absorbance of water at the absorption band has a vary large peak around 150 nm, the cell length for spectral measurement should be decreased as thin as a few hundred nanometers, and oxygen should be deleted in a measurement environment. However, for component analysis with a higher sensitivity it is necessary to measure a side portion from 160 to 180 nm where a change in spectral absorption becomes larger.

In order to measure far ultraviolet spectra of water or an aqueous solution around the absorption peak of water (150 nm), it is necessary to shorten the cell length as short as about 100 nm, but this is difficult. Then, the inventors pay attention to attenuated total reflection (ATR) method known as a method for measuring absorption spectra of a substance having very large absorption. In the far ultraviolet measurement methods for solute concentration in an aqueous solution, known before Japanese Patent laid open Publication 2005-214863, the concentration of a particular substance is determined according to the absorption band of the solute, not based on the spectral change in the spectra of water solvent. On the other hand, as will be explained below, the wavelength range for the above-mentioned measurement of solute concentration based on spectral change of water or solvent can be extended to 160 to 180 nm by using an optical probe for attenuated total reflection (hereinafter referred to as an attenuated total reflection optical probe) and an attenuated total reflection apparatus, so that the solute concentration can be measured at higher sensitivity.

Figure 3:
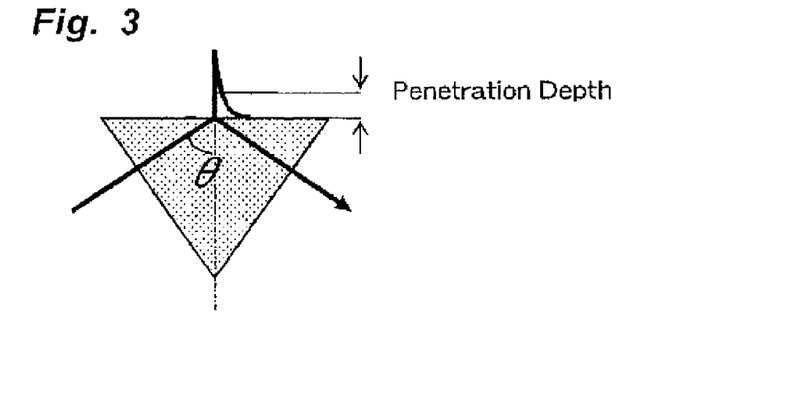
FIG. 3 is a diagram of a structure of a general attenuated total reflection optical probe.

The attenuated total reflection method is explained first. As shown in FIG. 3, there is an interface, shown at the upper side in the drawing, between a medium having a higher refractive index such as synthetic quartz and another medium having a lower refractive index (a sample medium to be measured, such as water). When a ray of light is incident on the medium having the higher refractive index, it is reflected totally if the incident angle θ is larger than the critical angle. However, at this time, the ray of light penetrates further into the medium having the lower refractive index by a certain depth of the order of wavelength, travels along the interface and is reflected thereafter. The light penetrating into the medium is called evanescent wave. The intensity of electric field of the evanescent wave is highest at the reflection point, and it attenuates steeply in a direction normal to the interface. The change in electric field intensity in the direction normal to the interface is shown in FIG. 3 schematically, and the depth at which the electric field intensity is decreased by a factor of 1/e is called penetration depth. In this method, optical absorption due to the penetration of light on total reflection or evanescent wave in the order of wavelength is measured from the reflected light. As the penetration depth of light corresponds to the optical path length for transmission spectra, absorption spectra similar to the transmission spectra for cell length of the order of wavelength can be obtained theoretically. The invention proposes to measure the reflection and absorption spectra with an attenuated total reflection prism in a wavelength range from 160 to 180 nm, in order to adapt to the above-mentioned restriction that cell length of a few hundred nanometers or smaller has to be used for a measurement of absorption spectra in the far ultraviolet region and the requirement that the wavelength range from 160 to 180 nm is important for a measurement of a very small concentration of a solute component in an aqueous solution.

An optical probe adaptable to the attenuated total reflection method has to satisfy following two conditions.
(a) The refractive index of the optical probe is larger than that of a sample substance (total reflection condition).
(b) The optical material of the optical probe is transparent or the transmittance is sufficiently high in a measurement wavelength range (transmission condition).

However, there is available no optical material which meets the above two conditions for the attenuated total reflection optical probe because the refractive index of water increases remarkably as the wavelength decreases. For example, a material such as quartz or sapphire having higher refractive index than water in the far ultraviolet region does not have sufficient transmittance around 160 nm, while a material such as magnesium fluoride or calcium fluoride which transmits far ultraviolet light has refractive index lower than water or does not satisfy the total reflection condition. Therefore, an optical probe is available for only above 200 nm or at best above 190 nm. Therefore, an attenuated total reflection measurement with an optical probe which can be used down to the peak wavelength around 150 nm has not been reported, including the prior art probes explained above in the background art.

Figure 4A:
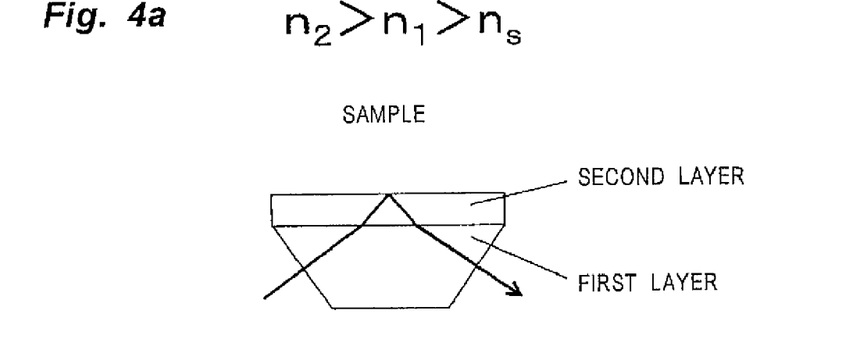
FIG. 4a is a diagram for explaining optical transmission and reflection in a two-layer structure.
Figure 4B:
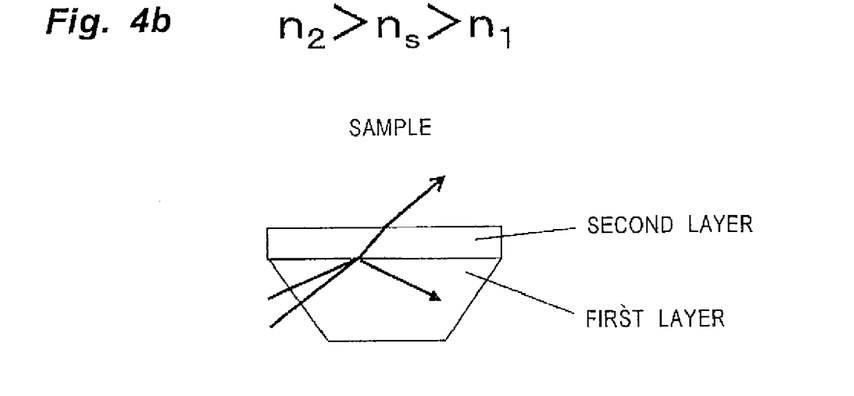
FIG. 4b is another diagram for explaining optical transmission and reflection in a two-layer structure.

Previously, an example is proposed of an attenuated total reflection optical probe of a flat two-layer structure made of a plurality of materials having different refractive indices. Refractive index $n_1$ of a first layer is lower than refractive index $n_2$ of a second layer, while, as shown in FIG. 4a, for attenuated total reflection at the interface, refractive index $n_1$ of the first layer has to be higher than refractive index $n_s$ of a sample. On the other hand, as shown in FIG. 4b, if refractive index $n_1$ of the first layer is lower than refractive index $n_s$ of a sample, attenuated total reflection does not undergo at the interface with the sample. In this case, when a ray of light, entering from the first layer to the second layer, is refracted in the second layer, but does not have an incident angle larger than the critical angle, so that it transmits and is refracted at the interface. That is, the light transmits from the first layer to the second layer, or it is reflected totally at the interface between the first and second layers without entering into the second layer. For example, Japanese Patent laid open Publication 2001-91710 shows an optical prism of a flat two-layer structure wherein a second layer made of a material having refractive index $n_2$ larger than refractive index $n_1$ of the material of the first layer is inserted between a sample and the first layer. However, in the condition that the refractive index $n_1$ of the material of the first layer is lower than refractive index $n_s$ of the material of the sample, the attenuated total reflection does not occur at the interface with the sample.

The inventors discover that absorption due to attenuated total reflection can be measured in a wavelength range shorter than 180 nm with an attenuated total reflection by imposing a particular combination condition on optical materials included in an optical probe made of a plurality of layers. Then, by using the probe, an apparatus for measuring water or an aqueous solution is provided, for example, for measuring very small concentration of a solute component in an aqueous solution, or for detecting very small change in water quality. By using the optical probe and the apparatus, spectral measurement can be performed with the attenuated total reflection method similarly on a substance, other than water, having large absorption in the far ultraviolet region.

An attenuated total reflection optical probe made of a composite layer has a combination of first and second components. The first component is made of a first optical material having an optical transmission property in the far ultraviolet region. The second component has an interface with the first component and a flat plane to be in contact with a sample, and it is made of a second optical material having refractive index $n_2$ higher than refractive index $n_s$ of a sample substance ($n_2 > n_s$). The second optical material has refractive index $n_2$ higher than refractive index $n_1$ of the first optical material ($n_2 > n_1$). The second optical material generally has transmittance lower than the first optical material, so that an optical probe cannot be fabricated only with the second optical material. A ray of light, entering into the first component, transmits the first component and is refracted at the interface between the first and second components to enter into the second component. Then it is reflected totally at the flat plane. The interface has a shape such that the ray of light can be incident on the flat plane with incident angle larger than the critical angle. A part of the light is reflected as evanescent wave after traveling the sample.

Figure 5:
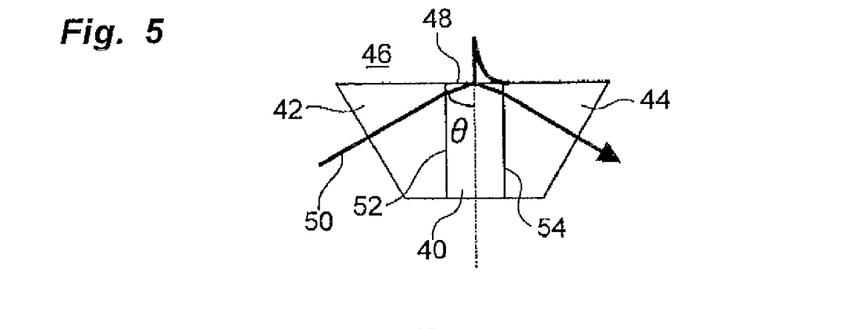
FIG. 5 is a diagram of a structure of an optical probe according to a first embodiment having a vertical three-layer structure.

FIG. 5 shows an optical probe of a vertical three-layer structure according to the first embodiment. The optical probe is made of a rectangular, higher refractive index optical material layer 40 and first and second holders 42 and 44 adjacent to the two sides thereof. A sample substance 46 makes contact with an end face 48 in the longitudinal direction of the higher refractive index optical material layer 40. The second optical material of the high refractive index optical material layer 40 to be in contact with water as a sample substance is required to have refractive index higher than that of water in a wavelength range down to around 160 nm. Materials meeting this requirement are, for example, synthetic quartz (or natural quartz) and sapphire. The internal transmittance (transmittance of the material itself without considering reflection loss) of quartz or sapphire of 1 mm of thickness is equal to or larger than 50% in the far ultraviolet region around 160 nm. Therefore, it is desirable that the thickness of the high refractive index optical material layer 40 is smaller than a few hundred μm, but it can be used practically up to about 1 mm of thickness. Optical materials such as magnesium fluoride (refer to FIG. 13), lithium fluoride and calcium fluoride have lower refractive index than quartz and sapphire in the vacuum ultraviolet region, but the optical transmission is not deteriorated at thickness above 10 mm. Therefore, the optical probe has a multilayer structure, wherein the holders 42 and 44 are made of an optical material having refractive index lower than that of the second optical material of the higher refractive index optical material layer 40 and has a sufficient transmission property in the ultraviolet region above 150 nm, and the second optical material adjacent to the holders has thickness enough to be operated in a total reflection optical probe (for example, the internal transmittance is at least 10% in the wavelength range from 160 to 250 nm). For example, if magnesium fluoride is used for the holders 42, 44, sapphire is used as the second optical material, and the sample substance is water, the refractive index is about 1.5, 2.2 and 1.6 for magnesium fluoride, sapphire and water, respectively, in a far ultraviolet range around 160 nm. Thus, an optical probe can be realized for measuring absorbance due to the attenuated total reflection in water or an aqueous solution around 160 nm. The ray of light 50 entering in the first holder 42 is incident on the interface 52 between the first holder 42 and the higher refractive index optical material layer 40 and is refracted. Then, it is incident on the end face 48 at an angle larger than the critical angle to be reflected totally. The reflected ray of light is refracted at the second interface 54 between the higher refractive index optical material layer 40 and the second holder 44, and goes out from the second holder 44. As shown in FIG. 4b, in a flat structure, if the refractive index of the first material is smaller than that of a sample in a flat structure probe, a ray of light incident on the higher refractive index optical material layer transmits the interface between the layer and the sample, and no total reflection occurs. However, this problem of a flat structure can be solved by using the above-mentioned structure wherein the interface 52 and the end face 48 are arranged perpendicularly to each other. The absorbance of the sample substance 46 is determined by measuring the reflected light. The outer shape of the first holder 42 is preferably designed such that a ray of light from the external is incident normally. The optical materials for the higher refractive index optical material layer 40 and the holders 42, 44 are explained later. An angle between the end face 48 and the interface 52, 54 of the higher refractive index optical material layer 40 is preferably right angle, but it is not necessarily so. Any angle may be used as far as the total reflection condition is met such that the ray of light entering from the holder into the higher refractive index optical material layer 40 is reflected totally at the interface with the sample. The angle may be any angle in a range between 90 degrees to the critical angle. By using the optical probe, an apparatus can be provided for measuring a very small concentration of a solute in an aqueous solution or the like.

Thus, the above-mentioned optical probe is made of the first components (holders) 42, 44 made of the first optical material having the optical transmission property and the second component 40 made of the second optical material adjacent to the first components 42 at the interfaces 52, 54. The second optical material has refractive index higher than a sample substance and the first optical material. The second component 40 has thickness so as to have internal transmittance equal to or higher than 10% at measurement wavelengths, and it has, at the side to be in contact with the sample substance 46, a plane 48 at which a ray of light having an incident angle higher than the critical angle is reflected totally.

Figure 6:
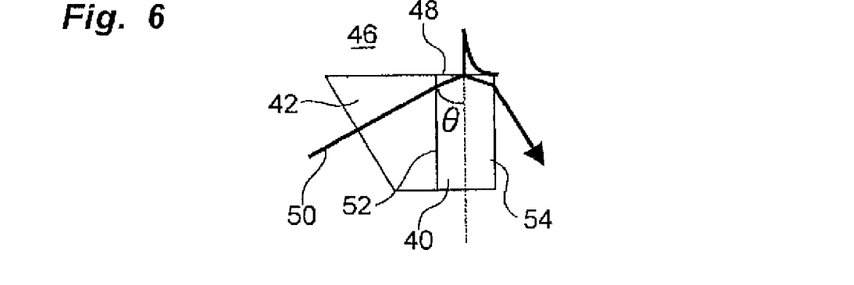
FIG. 6 is a diagram of a structure of a modified example of the optical probe shown in FIG. 5.

FIG. 6 shows a modified example of an optical probe according to the first embodiment. In the optical probe, the second holding member is omitted in contrast to the optical probe shown in FIG. 5. The ray of light 50 reflected at an end face 48 of the higher refractive index optical material layer 40 goes out through the interface 54 into air.

Figure 7:
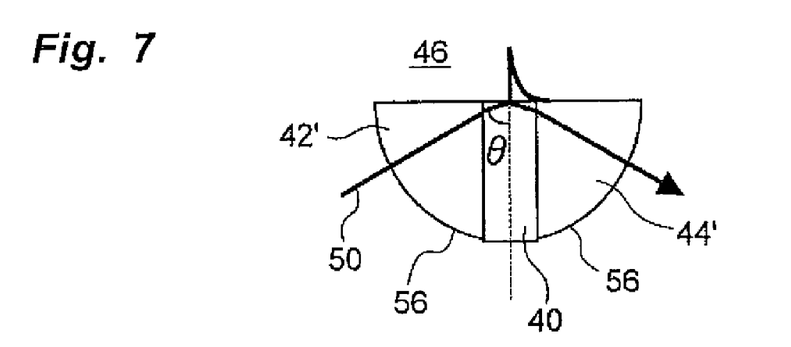
FIG. 7 is a diagram of a structure of another modified example of the optical probe shown in FIG. 5.

FIG. 7 shows another modified example of an optical probe according to the first embodiment. The outer shapes 56 of the first holding member 42' and the second one 44' are semicircular. Therefore, a ray of light can be incident normally to the holding member 42' even when the incident direction is changed.

Figure 8:
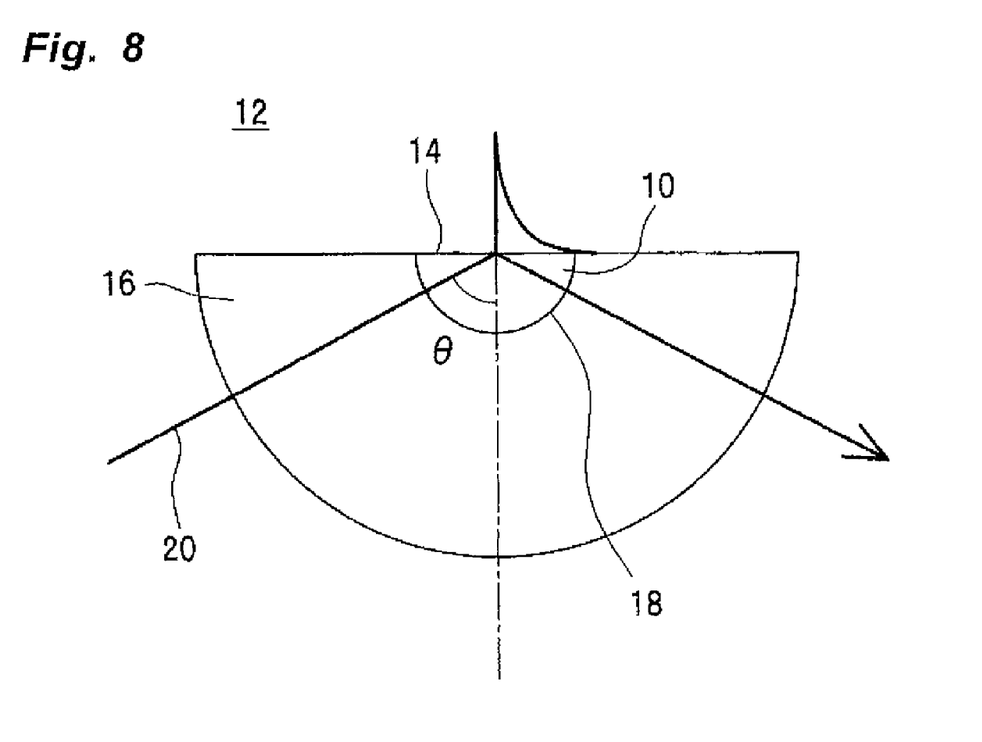
FIG. 8 is a diagram of a structure of an optical probe according to a second embodiment having a semicircular two-layer structure.

FIG. 8 shows an optical probe according to the second embodiment. The higher refractive index optical material layer 10 has an end plane to be in contact with a sample substance 12. The layer 10 contacts with the holder 16 at an interface 16 at the side of the layer 10, at a side not making contact with the sample substance 12. The outer shapes of the interface 18 and the holder 16 are semicircular. Therefore, a ray of light 20 is incident almost normally to the holder 16 and the interface 18 irrespective to the incident direction, and it can be incident on the interface 14 to be in contact with the sample substance at an incident angle larger than the critical angle. That is, in this structure, even if the interface plane between the holder 16 and the higher refractive index optical material layer 10 is not vertical to the interface plane 14 between the higher refractive index optical material layer 10 and the sample substance 12, a ray of light incident on the interface 14 can be reflected totally.

As shown in FIG. 8, the two layer structure optical probe according to the second embodiment has the holder 16 and the higher refractive index optical material layer 10 making close contact with a plane 18 of the holder 16. The higher refractive index optical material layer 10 having refractive index higher than a sample substance has a plane 14 to be in contact with the sample substance, and a ray of light can be reflected totally at the face 14. An angle of the plane 14 with the incident light 20 can be calculated preliminarily based on the difference of refractive indices of the sample substance and the higher refractive index optical material layer 10. The holder 16 is made of an optical material such as magnesium fluoride, lithium fluoride, calcium fluoride or the like. The shape of the holder 16 has a semicircular section in this example, but it is not limited thereto. For example, an interface portion for incident angles smaller than the critical angle can be removed as a flat plane if necessary. The ray of light 20 entering into the holder 16 transmits the holder 16 and comes straightly or is retracted at the interface 18 to enter into the higher refractive index optical material layer 10. The ray of light 20 transmitting the higher refractive index optical material layer 10 is incident on the plane 14 at an incident angle higher than the critical angle and is reflected totally. The reflected light 20 is incident on the next interface at an incident angle higher than the critical angle and is reflected totally, and it comes straightly or is refracted at the interface 18 into the holder 18, transmits the holder 16 and goes out to the external. By measuring the reflected light, the absorbance of the sample substance 12 is obtained.

The optical probe shown in FIG. 8 is explained further. The second component 20 made of the second optical material to be in contact with water as a sample substance should have refractive index higher than water in a wavelength range, for example, down to about 160 nm, similarly to the first embodiment. A material which satisfies this requirement is, for example, synthetic quartz (or natural quartz) and sapphire. Further, similarly to the first embodiment, the holder 16 of the probe is made of an optical material having refractive index smaller than the second optical material in the ultraviolet region above 150 nm and having a sufficient transmission property. When the optical path length transmitting the second optical material is sufficiently short to be 5 mm or smaller, the internal transmittance remains by about 10% even at around 160 nm, and the optical probe can be used barely as an attenuated total reflection optical probe even when the reflection loss at the plane at which the light comes in and goes out is taken into account. Then, a two-layer structure probe is provided by using the second optical material having thickness operable as a total reflection optical probe (for example, having an optical path length equal to or smaller than 5 mm in a wavelength range of 160 to 250 nm). For example, when the holder 16 is made of magnesium fluoride, the second optical material is made of sapphire, and the sample is water, the refractive indices of magnesium fluoride, sapphire and water are about 1.5, 2.2 and 1.6 at about 160 nm in the far ultraviolet region. Then, an optical probe for measuring attenuated total reflection for water or an aqueous solution at around 160 nm can be realized, and by using the probe, an apparatus can be provided for measuring a very small concentration of a solute in an aqueous solution.

As mentioned above, the two-layer structure optical probe is made of a semicircular first component (holder) 16 made of a first optical material having an optical transmission property in the far ultraviolet region under measurement (for example, a region of far ultraviolet wavelengths larger than 150 nm), and a semicircular second component 10 made of a second optical material in contact with the first component 16 at the interface 18. The second optical material has refractive index higher than those of a sample substance and the second component 10 in the far ultraviolet region, and the second component 10 has thickness having internal transmittance of at least 10% and has, at the side to be in contact with the sample substance 12, the end plane 14 totally reflecting an incident ray of light having an incident angle larger than the critical angle. The ray of light 20 is incident on the first and second components 16, 10 at an angle larger than the critical angle, is reflected totally at the interface 14 and goes out through the second and first components 10, 16.

Figure 9A:
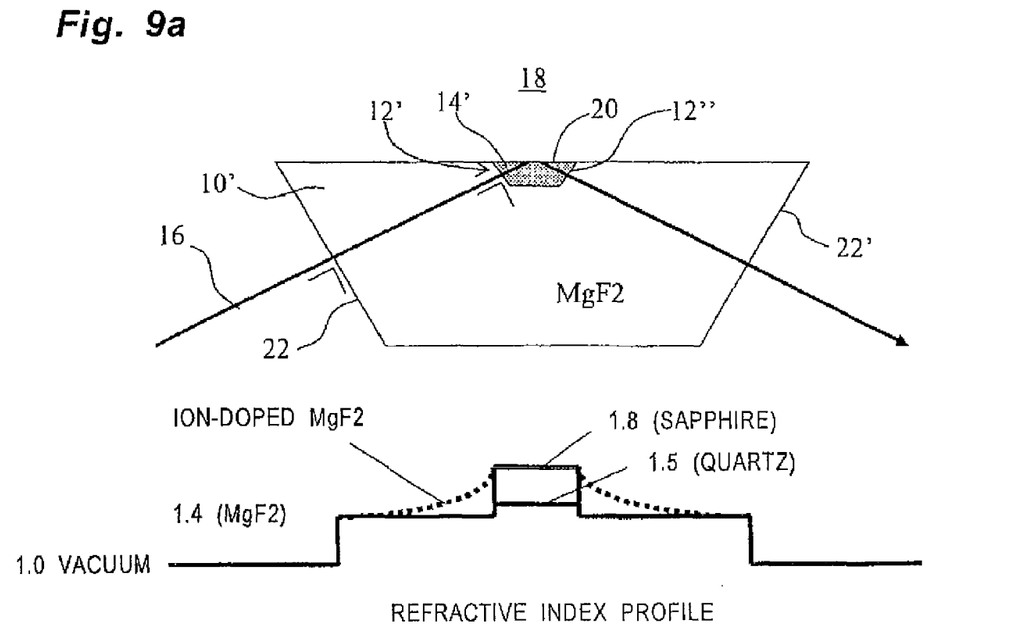
FIG. 9a is a diagram of a realistic optical probe arrangement and a refractive index profile.
Figure 9B:
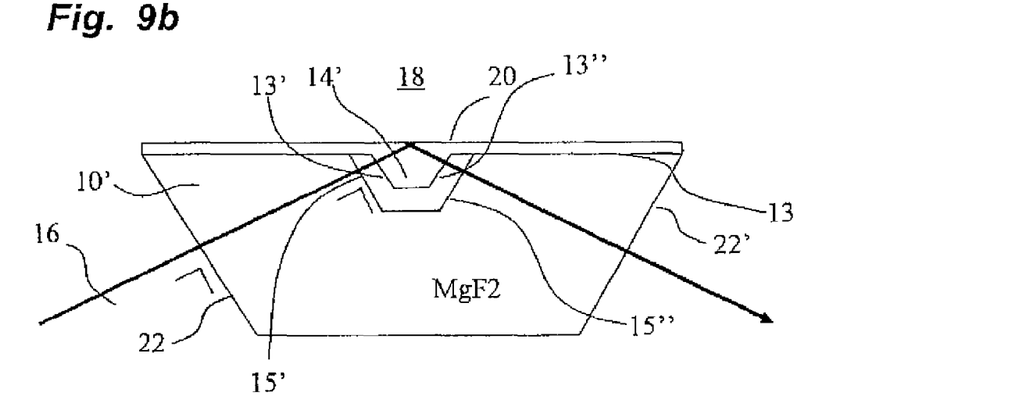
FIG. 9b is another diagram of a realistic optical probe arrangement and a refractive index profile.

FIG. 9*a* shows a structure of an optical probe of a modified example of the second embodiment and a refractive index profile thereof. The optical probe has, similarly to the optical probe of the first embodiment, a first component (holder) 10' made of a first optical material having an optical transmission property in the far ultraviolet region, such as magnesium fluoride, lithium fluoride, barium fluoride or the like, and a second component 10' made of a second optical material, such as synthetic quartz, sapphire or the like, adjacent to the first component 10' at the interface 18. The second optical material has refractive index higher than water in the ultraviolet region. The optical probe is different from that shown in FIG. 8 in that interfaces 12', 12" between the first and second components 10', 14' have shapes which make normal incidence of incident and reflected rays of light possible and that the ray of light having an incident angle larger than the critical angle is reflected totally at the interface 20 between the second component 14' and the sample substance 18. The thickness of the second component 14' is set to have a sufficient transmission property. The above-mentioned normal incidence decreases reflection loss when light is incident on the second component 14'. Further, an anti-reflection coating is applied on the interfaces 22, 22' having large gaps of refractive index. When the second component 14' is made of sapphire, it is desirable further to apply antireflection coatings to the interfaces 12, 12', as a structure shown in FIG. 9*b*. In this case, the first component 10' is held on the face 13' of the second component 14', and end planes 13', 13", 15' and 15" are positioned in an environment to be purged with nitrogen (or in vacuum), and they are subjected to antireflection coatings. Further, the planes 22, 22' of the first component 10' have shapes for normal incidence. The total reflection occurs at the plane of the second component to be in contact with the sample substance 18. The evanescent wave travels along the plane. By measuring the reflected waves, the absorption in the sample substance is measured. Thus, the reflected wave is affected by the transmission into the sample substance 18 such as water or an aqueous solution. Further, when a higher refractive index optical material portion is formed, as in the third embodiment to be explained later, by using surface modification with ion doping in $MgF_2$, it is designed to have refractive index having a gradient in a direction along which the light ray propagates. In the drawing of refractive index profile, refractive index is shown along the light ray 16 when the first optical material is magnesium fluoride and the second optical material is quartz or sapphire. Further, it is shown how the refractive index changes when the optical material of magnesium fluoride is subjected to surface modification with ion doping.

Figure 10:
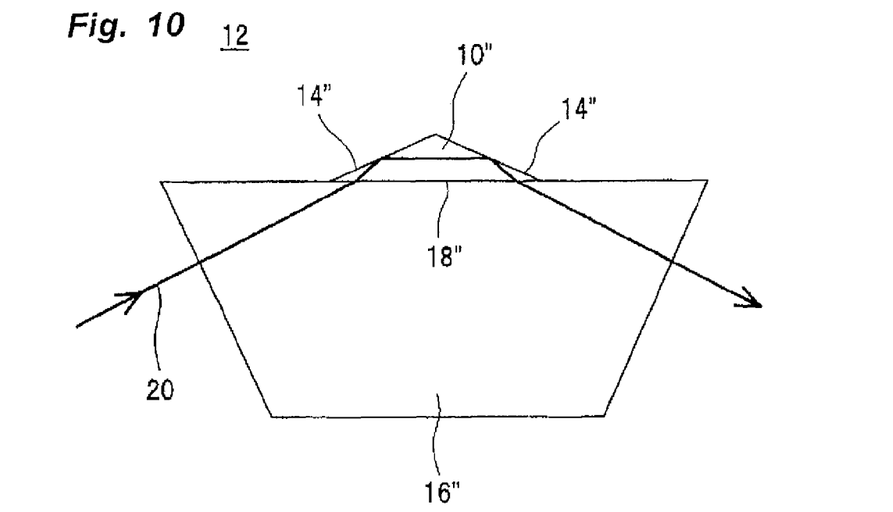
FIG. 10 is a diagram of another structure of an optical probe according to the second embodiment having a two-layer structure.

FIG. 10 shows a modified example of an optical probe of a two-layer structure according to the second embodiment. The optical probe has a structure wherein a second component 10' having an isosceles triangle section is adhered to a face of a first component 16'. The first component 16' and the second component 10' are adhered to each other with optical contact or thermal bonding. Therefore, the second component 10' makes contact with the first component 16' so that the base of the isosceles triangle becomes the interface with the first component 16', so that the two equal sides of the isosceles triangle make contact with the sample substance. A ray of light 20 transmitting the first component 16', entering through the interface 18' into the second component 10', is reflected totally at the two interfaces 14' adjacent to the sample, and comes into the first component 16' and goes out therefrom again.

Figure 11:
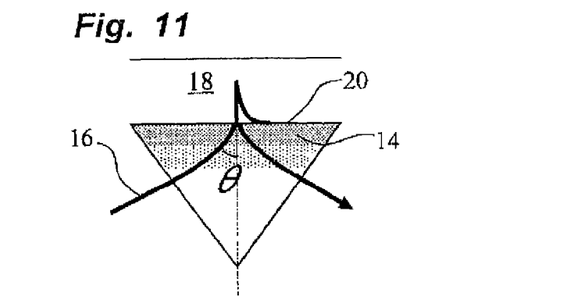
FIG. 11 is a diagram of a structure of an optical probe having a modified surface.

In an optical probe according to a third embodiment, an optical probe 14' is made of an optical material such as magnesium fluoride having an optical transmission property in the far ultraviolet region, and refractive index changes continuously at least in a part of the optical probe, as shown in FIG. 11. By modifying a portion near the surface to be in contact with a sample substance 18, the refractive index is increased continuously, as shown schematically in FIG. 18 at the right and top side. The refractive index near the surface becomes higher than that in the other part, and it becomes higher on the flat plane 20 than that of the sample substance 18 finally. In the example shown in FIG. 11, a ray of light reaches to the surface along an arc or ellipse orbit. For example, ion doping can be used for surface modification. For example, metallic ions of aluminum, magnesium or sodium can be distributed in the surface of a material, such as magnesium fluoride, lithium fluoride, calcium fluoride, barium fluoride or the like which transmits vacuum ultraviolet light, so as to be distributed in a certain concentration range by using thermal diffusion or injection in a concentration range. Then, the concentration of embedded impurities is changed continuously, so that the refractive index is also changed continuously. Such surface modification is known as ion doping, ion implating or the like, and the refractive index in 150-180 nm can be increased intentionally. An optical prove for attenuated total reflection can be provided by changing the refractive index in the wavelength region in the flat plane 20 to be in contact with the sample substance 18 higher than the refractive index of water. Because impurities are distributed only in a very small thickness portion near the surface, though the transmittance is decreased, the optical probe can be used sufficiently for the attenuated total reflection method.

Figure 12:
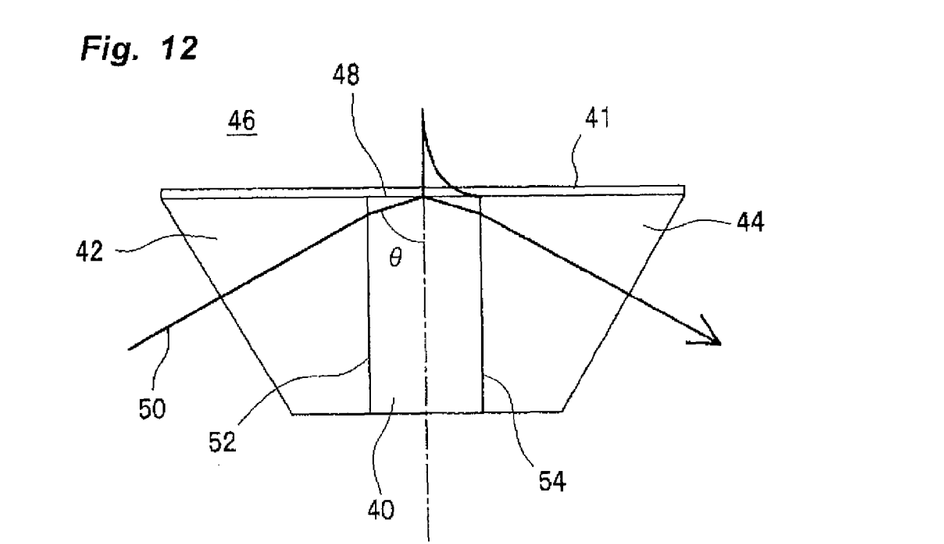
FIG. 12 is a diagram of an optical probe wherein the refractive index is changed continuously.

Next, a coating type optical probe as a modification of the above-mentioned embodiment is explained. If the optical material for the higher refractive index optical material layer 14 is sapphire in the optical probes according to the first and second embodiments, or it surface modification is performed with ion doping in the optical probe according to the third embodiment, a part of the optical material is liable to be dissolved into water or the sample as impurities. Especially when the sample is water for washing a semiconductor, the dissolution of impurities is a big problem. In order to prevent the dissolution, a third layer is formed on the surface 48 to be in contact with the sample substance, as shown in FIG. 12, with use of a material such as synthetic quartz or natural quartz which does not dissolve into the sample substance. Because the refractive index of the optical material is larger than that of quartz, the incident ray of light is reflected totally at the interface 48 between the optical material and the coating layer 41 on quartz. If the thickness of the coating layer 41 is sufficiently thinner than the measurement wavelength (about a few tens nm), the light (the evanescent wave) penetrates into the sample, and the absorbance of the sample can be measured.

Figure 13:
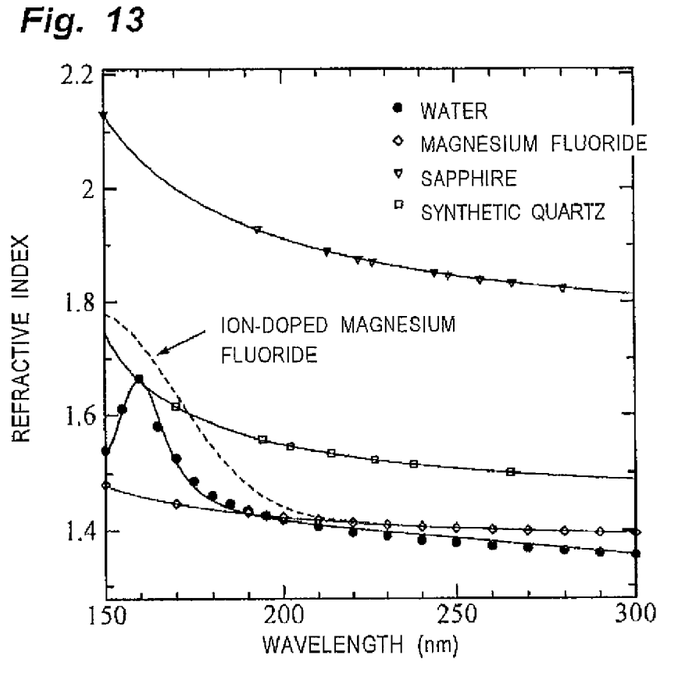
FIG. 13 is a graph of the wavelength dependence of refractive index of optical materials in the far ultraviolet region.

FIG. 13 shows the wavelength dependence of refractive indices of various materials, that is, sapphire, synthetic quartz or natural quartz ($SiO_2$), magnesium fluoride and water. The solid lines represent suitable approximation functions created for the calculation.

Some calculation results and experimental data on some optical probes are explained below.

Figure 14:
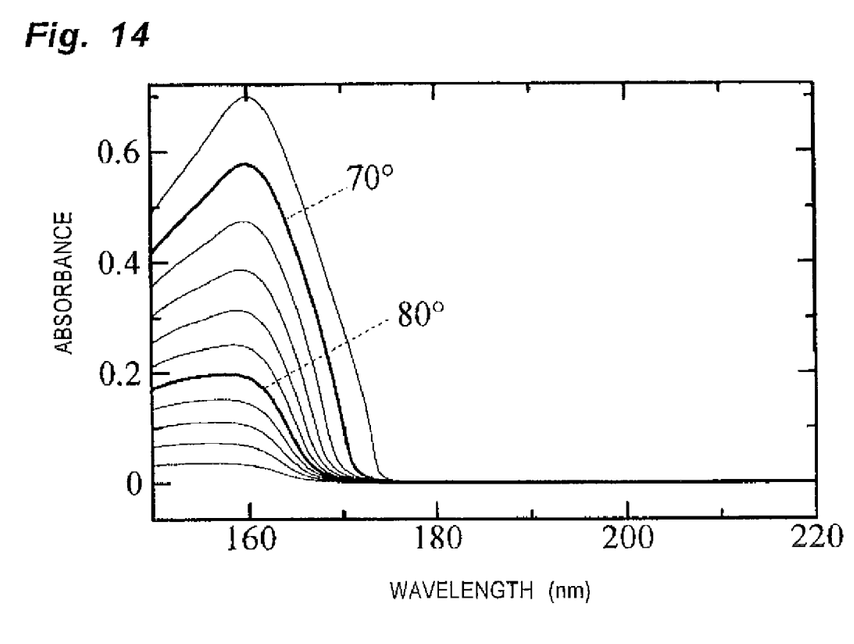
FIG. 14 is a graph of absorbance of an optical probe made of synthetic quartz plotted against incident angle.
Figure 15:
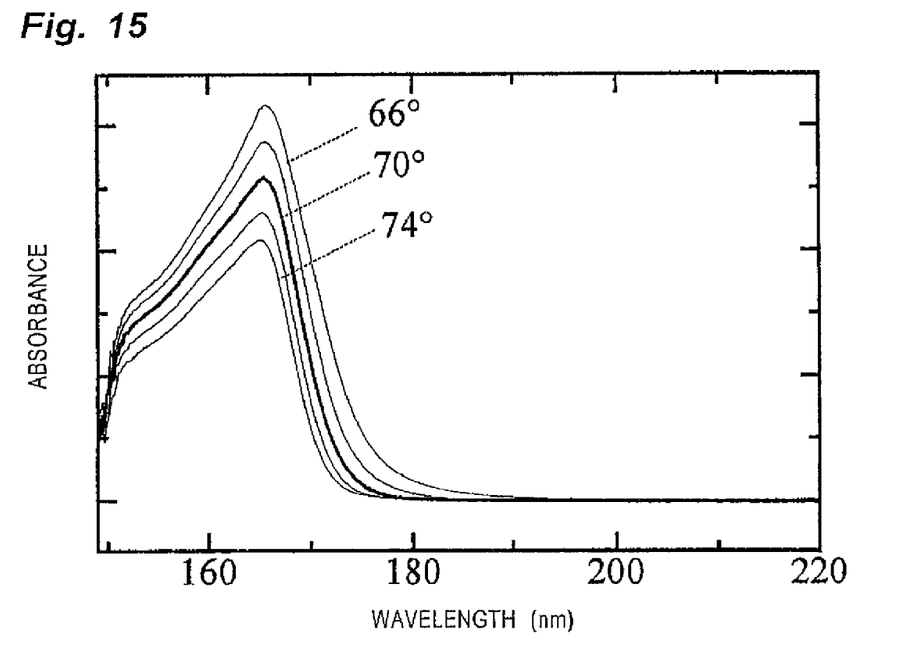
FIG. 15 is a graph of experimental data of absorbance of an optical probe made of synthetic quartz plotted against incident angle.

FIG. 14 shows calculated data on the incident angle dependence of the absorbance of pure water measured with the optical probe of a vertical three layer structure according to the first embodiment. Quartz is used as the optical material for the higher refractive index optical material layer. The peak of the absorbance decreases with increase in incident angle $\theta$ from 68°. If quartz is used as the optical material also for the higher refractive index optical material layer in the second embodiment, a similar result is obtained for an optical probe. FIG. 15 shows experimental data of the incident angle dependence of absorbance of pure water obtained with the optical probe according to the first embodiment of a vertical three layer structure. Synthetic quartz is used as the optical material for the higher refractive index optical material layer. The peak of the absorbance decreases with increase in incident angle $\theta$ from 68°, and this is consistent with the above-mentioned calculation data. The position of the absorption maximum is shifted to a higher wavelength than in the calculated data, but this is ascribable to a phenomenon wherein the refractive index of synthetic quartz comes very close to or becomes lower than that of pure water at around 165 nm, so that a part of the light is not reflected totally and transmits into pure water. As a result, an apparent absorption maximum occurs at about 165 nm. However, absorption spectra of water can be obtained in a wavelength range below 180 nm not yet measured before.

Figure 16:
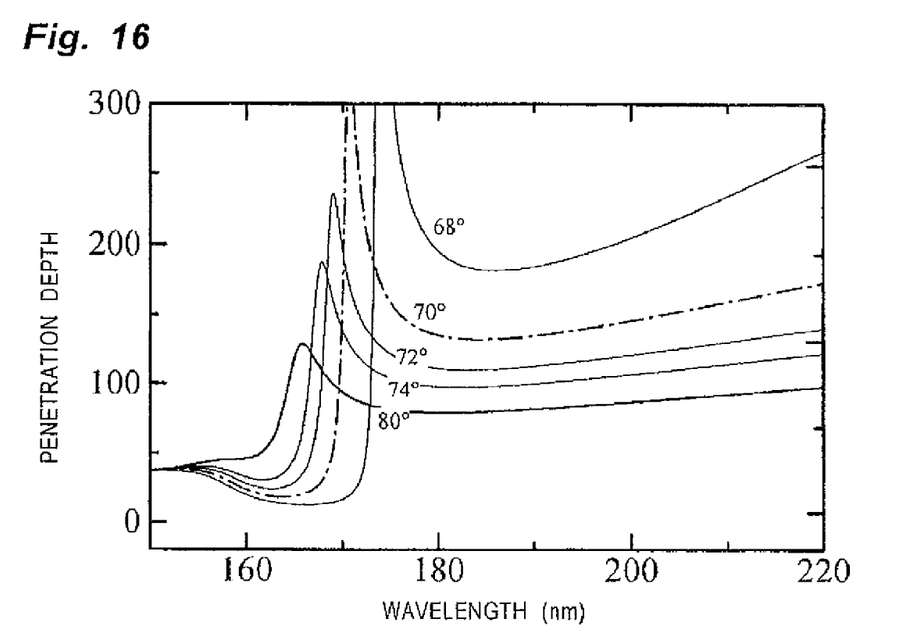
FIG. 16 is a diagram of penetration depth of evanescent wave of an optical probe made of synthetic quartz.

FIG. 16 shows the wavelength dependence of penetration depth (calculation result) when the higher refractive index optical material in an optical probe in the first or second embodiment is quartz. The penetration depth decreases with increase in incident angle $\theta$ from 68°. There is a wavelength at which the penetration depth has a maximum due to the dispersion in the optical material. This shifts the maximum position of absorption spectra obtained by the total reflection optical probe towards a shorter wavelength than the actual maximum peak position of water (estimated to be at about 150 nm). However, such change in absorption spectra is not a problem in quantitative measurement of very small amounts of solute components. At incident angle $\theta$ of 80°, the penetration depth is 50 to 100 nm at wavelengths around 160 nm. This corresponds to optical path length in a conventional optical cell.

Figure 17:
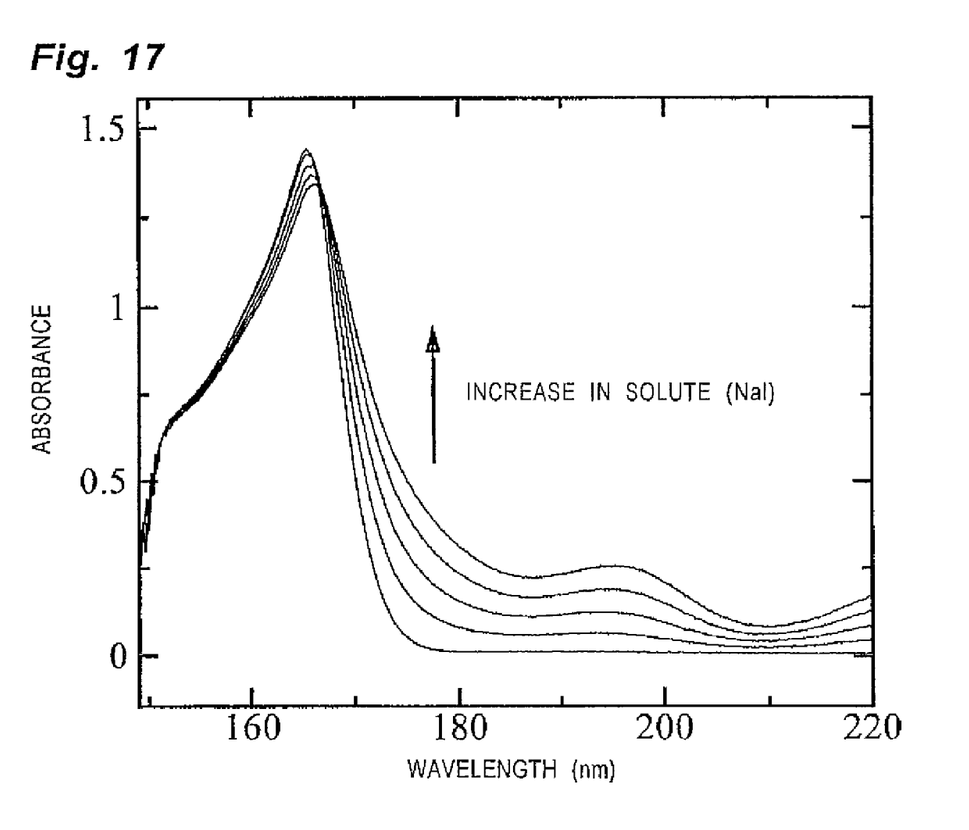
FIG. 17 is a graph of experimental data of absorbance of an optical probe made of synthetic quartz plotted against solute concentration.

FIG. 17 shows measurement data (experimental result) of spectra and absorbance in aqueous solutions of different solute concentrations when the optical material of the higher refractive index optical material layer is quartz in an optical prove of a vertical three-layer structure according to the first embodiment. The incident angle is 70°. An absorption peak due to NaI solute is observed at around 195 nm. With increase in solute concentration, the absorption peak rises up, and the absorption band of water is shifted towards the longer wavelength side in the wavelength range below 180 nm. By analyzing the shift quantitatively, analysis with a higher sensitivity can be realized than the analysis based on the absorption band inherent to the solute. Similar results can be obtained in the second embodiment if the higher refractive index optical material layer is made of quartz.

Figure 18:
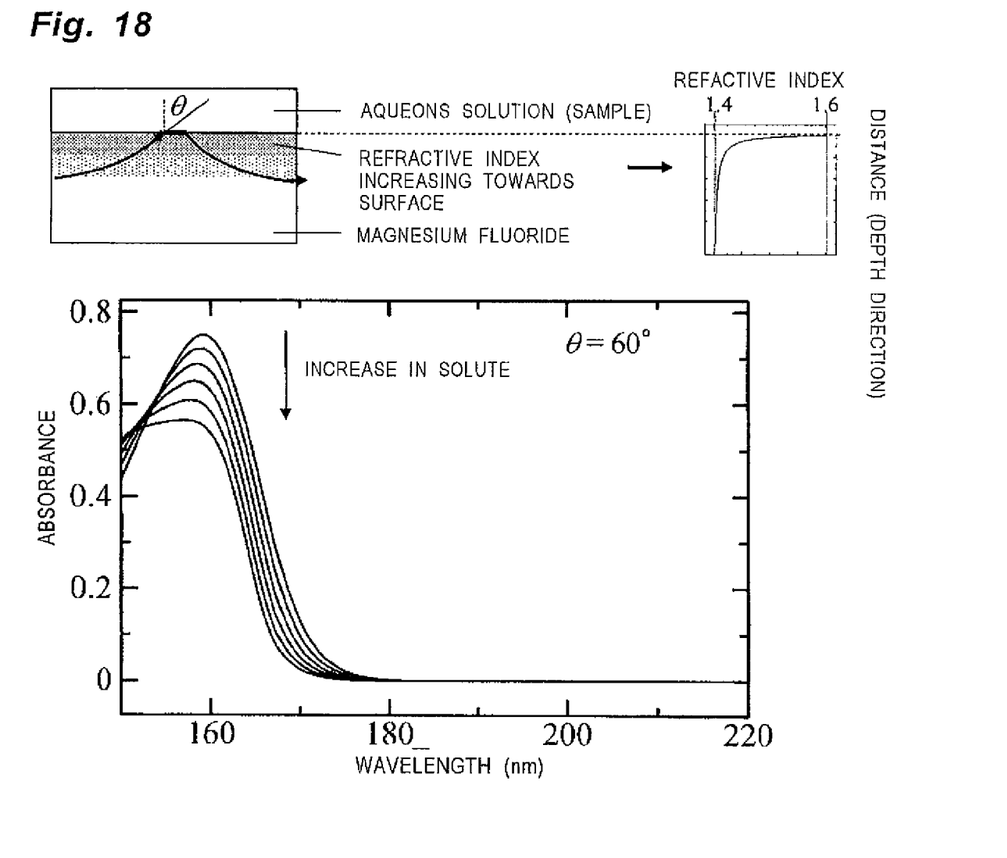
FIG. 18 is a graph of absorbance of an optical probe with a modified surface plotted against solute concentration.

In the optical probe according to the third embodiment wherein the surface of magnesium fluoride as the optical material is modified, a ray of light reaches to the surface along an arc or eclipse orbit when the refractive index is assumed to distribute as shown in the top-and-right side in FIG. 18. FIG. 18 shows data (calculation result) of absorbance of aqueous solutions having different solute concentrations measured with the optical probe of this structure.

Figure 19:
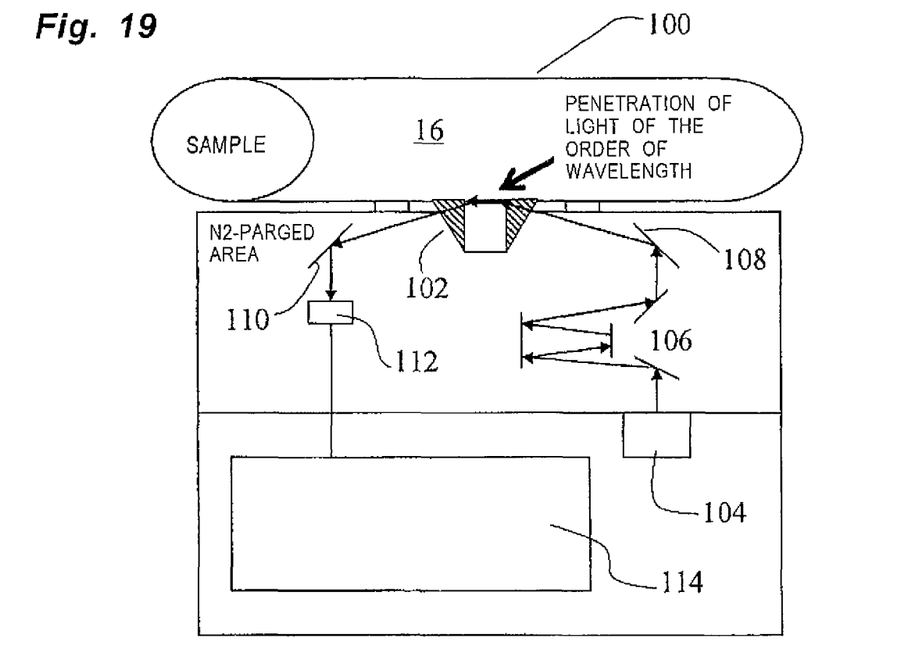
FIG. 19 is a block diagram of a densitometer using far ultraviolet spectra for components of very small amounts.

FIG. 19 shows a block diagram of a densitometer using far ultraviolet spectra for measurement wavelengths 160-210 nm. The densitometer can be used as a spectroscopic apparatus for an aqueous solution. An optical probe 102 is set to contact with the sample substance 18 in a sample path 100. A sample substance may be introduced in a cell so as to make the optical probe face the sample substance in a cell. Alternatively, a wall plane of a pipe for introducing a sample may be used as a probe, without using a cell. Light emitted from an ultraviolet light source 104 such as a deuterium lamp transmits a grating mirror 106 as a monochromator and is reflected by a mirror 108 to enter into the optical probe 102. The incident angle to the optical probe 102 is set appropriately. The light reflected from the optical probe 102 is reflected by a mirror 110 and enters into an ultraviolet sensor 112. In the above-mentioned optical system, nitrogen gas is introduced in order to purge oxygen gas from the optical system. Alternatively, air may be replaced with argon gas, or the air itself may be evacuated. The spectra detected by the ultraviolet sensor 112 are processed by a signal processor 114 to calculate the absorbance based on the measured data. Then, a calibration line can be created with a known multivariate analysis on the absorbance data at a plurality of wavelengths. In order to measure water spectra at 160 nm, cell length of about 100 nm is necessary when a cell is used, while by using the attenuated total reflection optical probe, a very small cell length can be realized substantially, and the absorption peak of water can be measured at a high sensitivity. Further, the measurement can be performed real time. Because only a very small part of the sample substance near the interface is subjected to the exposure of ultraviolet light, degeneration of the sample due to radiation of ultraviolet light can be avoided substantially.

Figure 20:
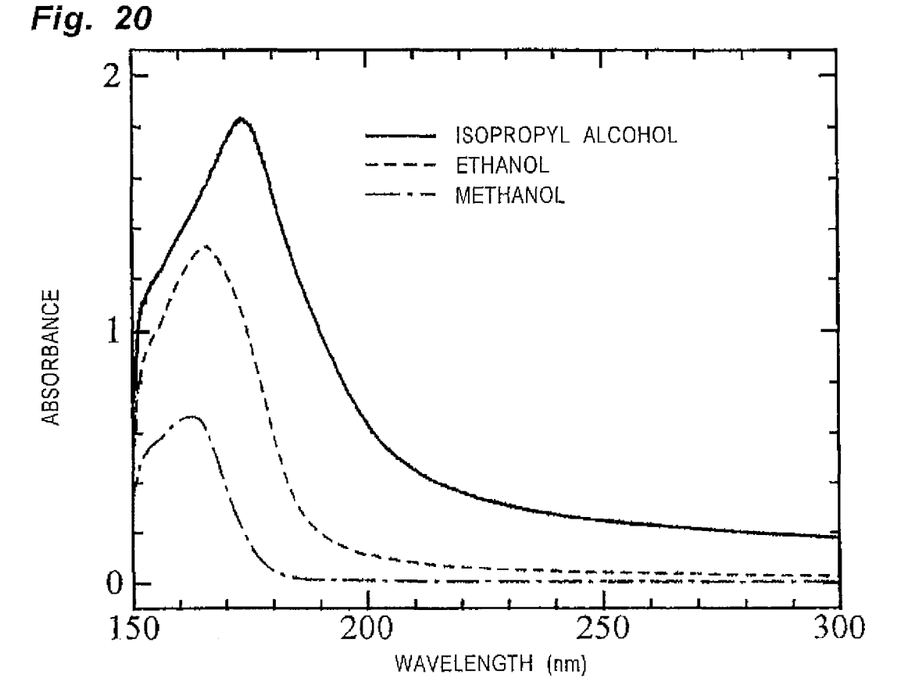
FIG. 20 is a graph of spectra of substances other than water.

As will be understood easily by a person skilled in the art, the above-mentioned optical probes are used for attenuated total reflection technique for liquid, gas and solid samples, other than water, having large absorbance in the far ultraviolet region. For example, the liquid sample may be isopropyl alcohol, and the gas sample may be oxygen. FIG. 20 shows examples of spectra of methanol, ethanol and isopropyl alcohol measured with a probe using sapphire as the optical material of the higher refractive index material layer.

The invention claimed is:

1. An attenuated total reflection optical probe comprising:
    a first component made of a first optical material transparent in a far ultraviolet region and having refractive index lower than a medium to be measured or a sample substance;
    a second component having an interface in contact with the first component and a flat plane in contact with the sample substance, the second component being made of a second optical material having a transmittance lower than the first component in the far ultraviolet region and having refractive index higher than the medium to be measured;
    wherein the interface between the first and second components has a form that a ray of light transmitting through the first component enters the second component and is incident on the flat plane of the second component at an incident angle equal to or larger than critical angle.

2. The attenuated total reflection optical probe according to claim 1, wherein the flat plane and the interface of the second component are perpendicular to each other.

3. The attenuated total reflection optical probe according to claim 2, further comprising a third component made of a third optical material transparent in the far ultraviolet region, wherein the third component is positioned opposite to the first component relative to the second component.

4. The attenuated total reflection optical probe according to claim 1, wherein the interface is semicircular.

5. The attenuated total reflection optical probe according to claim 1, wherein the interface has an in-coming plane through which light incident on the plane transmits, and an out-going plane through which a light reflected at the plane transmit.

6. The attenuated total reflection optical probe according to claim 1, wherein the second component has a section of an isosceles triangle, the base of the isosceles triangle makes contact with the first component as an interface with the first component, and the two isosceles sides thereof make contact with the sample substance.

7. The attenuated total reflection optical probe according to claim 1, wherein the first optical material is selected in a group of magnesium fluoride, lithium fluoride and calcium fluoride, and the second optical material is selected in a group of synthetic quartz, natural quartz, sapphire, zinc selenide and diamond.

8. The attenuated total reflection optical probe according to claim 1, further comprising an anti-reflection coating layer at least on one of the plane of the first component in which light comes in and goes out and the interface between the first and second components.

9. The attenuated total reflection optical probe according to claim 1, further comprising a coating layer on the plane in contact with the sample substance, the coating layer having thickness smaller than measurement wavelength.

10. A spectrometer for an aqueous solution comprising:
    an attenuated total reflection optical probe according to claim 1;
    a light source irradiating far ultraviolet light towards the probe;
    an optical sensor for detecting light totally reflected from the probe; and
    a spectroscopic element for far ultraviolet light, provided in an optical path from the light source and the optical sensor.

11. The attenuated total reflection optical probe according to claim 1, wherein an optical absorption of said medium or sample due to the penetration of light on total reflection is measured from light reflected at said flat plane.

12. The attenuated total reflection optical probe according to claim 1, wherein an optical absorption of said medium or sample is measured using an evanescent wave in said medium or sample generated by said ray of light, and a penetration depth of said light into said medium or sample corresponds to an optical path length for a transmission spectrum for a cell length of the order of a wavelength of said light.

13. The attenuated total reflection optical probe according to claim 1, wherein
    the first optical material is selected from the group consisting of magnesium fluoride, lithium fluoride and calcium fluoride, and
    the refractive index varies in a portion of said optical probe, wherein the portion in which the refractive index varies is formed with diffusion or injection of impurity ions.

* * * * *